(12) United States Patent
Perrut et al.

(10) Patent No.: US 6,204,401 B1
(45) Date of Patent: Mar. 20, 2001

(54) PURIFYING POLYUNSATURATED FATTY ACID GLYCERIDES

(75) Inventors: Michel Perrut, Nancy; Wieslaw Majewski, Le Méridien, both of (FR); Harald Breivik, Skjelsvik (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 09/355,303

(22) PCT Filed: Jan. 26, 1998

(86) PCT No.: PCT/NO98/00025

§ 371 Date: Sep. 27, 1999

§ 102(e) Date: Sep. 27, 1999

(87) PCT Pub. No.: WO98/32819

PCT Pub. Date: Jul. 30, 1998

(30) Foreign Application Priority Data

Jan. 28, 1997 (GB) .................................. 9701705

(51) Int. Cl.⁷ ....................................................... C11B 3/14
(52) U.S. Cl. ............................................ 554/205; 554/206
(58) Field of Search ..................................... 554/206, 205

Primary Examiner—Deborah Carr
(74) Attorney, Agent, or Firm—Fitzpatrick, Cella, Harper & Scinto

(57) ABSTRACT

A composition containing polyunsaturated fatty acid glycerides is purified by means of supercritical fluid fractionation in one or more countercurrent columns operated either with internal reflux achieved by a temperature gradient along the column or with an external reflux achieved through external regulation of the pressure, and using as the solvent a mixture of supercritical $CO_2$ and a polar co-solvent. Oligomeric and malodorous impurities in particular can be successfully removed by this process, which also can, if desired, be followed, or preceded, by another supercritical fluid fractionation with supercritical $CO_2$ under conditions adjusted so as to favor fractionation of the glyceride components.

15 Claims, 6 Drawing Sheets

PURIFYING POLYUNSATURATED FATTY ACID GLYCERIDES

Figure 1:
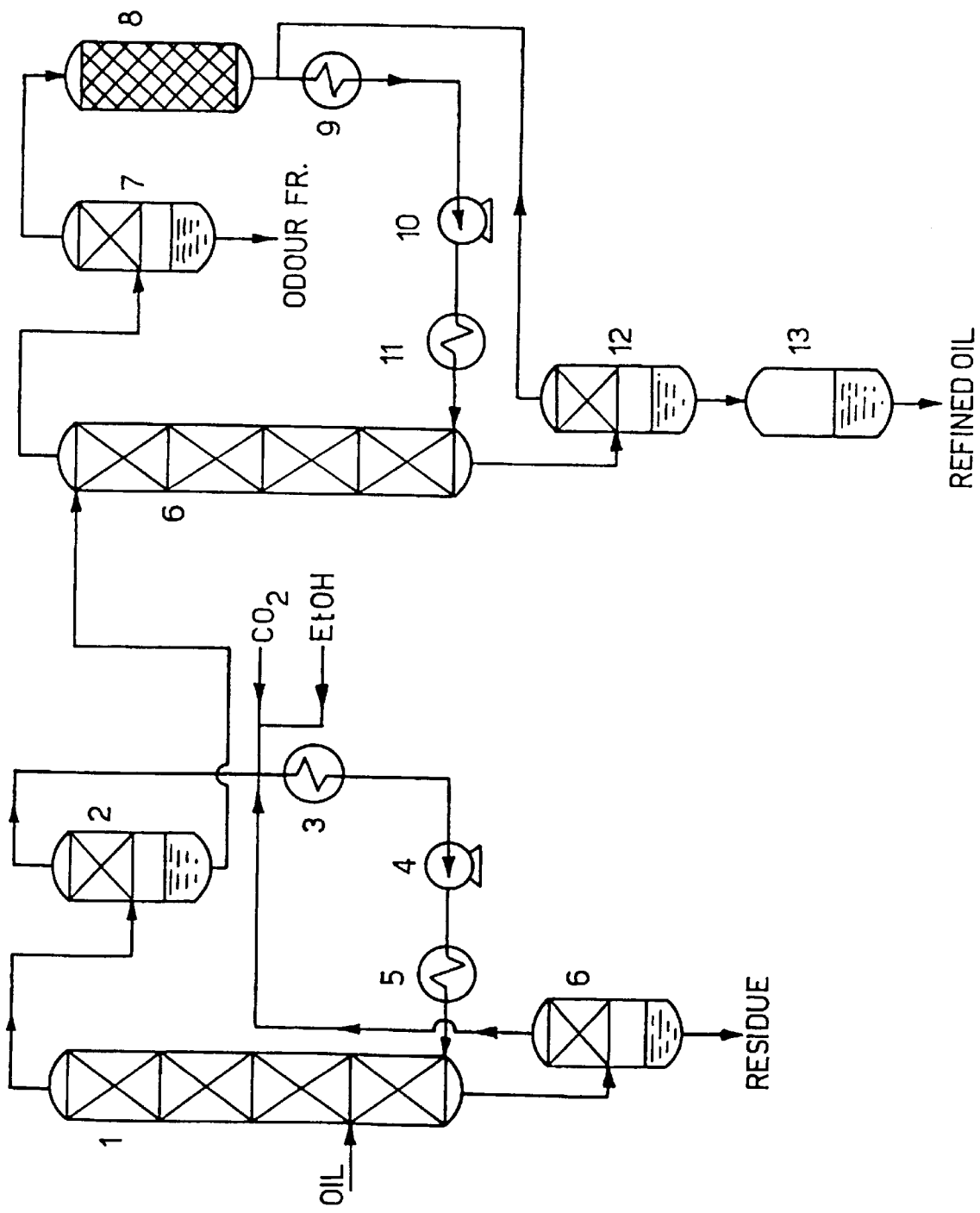

This application is a 371 of PCT/No 98/00025 filed Jan. 26, 1998.

This invention relates to a process for treating compositions containing polyunsaturated fatty acid glycerides in order to recover a purified polyunsaturated fatty acid glyceride product therefrom.

The fractionation of fatty acids and their derivatives has been widely investigated in recent years. The reason for this interest lies in the recognition that some fatty acids, especially long chain polyunsaturated fatty acids, are precursors for so-called prostanoid compounds, including prostacyclins and prostaglandins, which play an important role in the regulation of biological functions such as platelet aggregation, inflammation and immunological responses.

In this specification polyunsaturated fatty acids are identified according to the system wherein the omega- or n-number denominates the position of the first double bond when counting from the terminal methyl group, e.g. in an omega-3 or n-3 fatty acid, the first double bond occurs at the third carbon atom from the terminal methyl group of the acid. Further, when a fatty acid is identified, for instance, as C18:3, this refers to a fatty acid having 18 carbon atoms in the chain and three double bonds.

Two commercially important polyunsaturated omega-3 fatty acids, EPA (eicosapentaenoic acid, C20:5) and DHA (docosahexaenoic acid, C22:6) are found in marine oils. The biological properties of these fatty acids have been discussed in many publications and patents, such as for instance GB 2221843 which teaches that concentrated mixtures of EPA and DHA are efficient products for the treatment and prophylaxis of multiple risk factors for cardiovascular diseases.

Correspondingly, the polyunsaturated fatty acids of the omega-6 series, such as linolenic acid and arachidonic acid, are also of growing commercial importance. The omega-6 acids are commonly produced from vegetable oils such as evening primrose oil and borage oil and are widely employed for pharmaceutical purposes.

These polyunsaturated fatty acids are found in marine and vegetable oils mainly as triglycerides.

As such triglycerides usually also contain unwanted fatty acids, it is often necessary to cut the triglycerides to obtain the fatty acids either in free acid form or as esters with monofunctional alcohols such as methanol and ethanol in order that a proper separation of the desired fatty acids from the unwanted fatty acids can then be accomplished.

On the other hand, for many commercial purposes it is desired that the polyunsaturated fatty acids should be used in the form of glycerides. Accordingly, it is common practice to reconvert purified fatty acids back to glyceride form by esterification with glycerol, or transesterification with glycerol if the fatty acids are present as monofunctional esters. The resulting glyceride products will be termed "synthetic glycerides" hereinafter, to distinguish them from the "natural glycerides" found in the original marine or vegetable oils, although of course they themselves have originated from natural sources as well.

Polyunsaturated fatty acids are extremely fragile when subjected to heat or light in the presence of oxygen and will readily undergo rapid isomerization, peroxidation and oligomerization reactions. Accordingly, even if great care is taken at all times during the manufacture of purified fatty acid glycerides for commercial use, it is almost impossible to avoid several types of organic impurities being present in either the natural or the synthetic glyceride products, eg in particular:

(1) oligomers of fatty acids, which normally are absent from natural products but typically present up to 3–5 weight percent, and sometimes at even higher levels, in synthetic products (they are formed particularly during the esterification or transesterification with glycerol), (2) malodorous compounds giving an unpleasant smell and mainly consisting of aldehydes and other carbonyl compounds resulting from the breakdown of peroxides, and (3) a wide variety of coloured decomposition products which have not been fully defined by chemical analysis but which typically impart a darker colour to synthetic glycerides than to natural glycerides.

Over the past decade a number of scientific groups have focused on the effect of oligomeric (often called "polymeric") oxidation products on oil quality and on health. See, for example, Nawar et al "Stability of Fish Oils", N-3 News, 1988, 3:3; Kragballe et al "Polyumaettede fedtsyrepraeparater pa det danske marked. Sammensetning og oksidativ stabilitet", Ugeskr. Laeger, 1990, 152:894–897; and Hanmann "What's in those capsules", Inform, 1990, 1:117–120. It is generally recognized that the presence of such comparatively large concentrations of these impurities is undesirable.

For these reasons it would be desirable to reduce the oligomer (polymer) content of both natural and synthetic fatty acid triglycerides to less than 1% by weight, preferably to less than 0.5% by weight.

The malodorous fatty aldehyde and other carbonyl components are responsible for the very unpleasant odour of many oils—they give the very typical "fishy" smell to marine oils, for example—and prevent these oils being directly usable in dietary and cosmetic products and even restrain their pharmaceutical utility. For this reason it is conventional to steam deodorise fatty acid glyceride compositions. However, this process has to be conducted at relatively high temperatures and can, by itself, give rise to the further production of oligomeric material (see Hanmann, supra). Moreover, it should also be noted that deodorising does not completely remove all oxidation/decomposition products. According to the authoritative Bailey's Industrial Oil and Fat Products (ed. Y. H. Hui, John Wiley & Sons, Inc., New York, 5 ed. 1996, Vol. 4, page 51): "While the deodorizer generally represents the final step in edible oil processing, and can make a good product from a less than perfect feedstock, the deodorizer cannot forgive the sins made in earlier processes. While the primary products of oxidation are removed (as indicated by the peroxide value), several damaged oil may contain secondary products of oxidation (measured as anisidine value).".

The coloured by-products result in the fatty acid glycerides having an unpleasant appearance. Moreover, it is unsatisfactory to distribute products containing contaminants which have not been completely characterised chemically, particularly in the health or drug fields.

Metal compounds are often used as catalysts in the production of synthetic polyunsaturated fatty acid glycerides, and typically include zinc, silver, mercury and calcium as their salts or oxides. Residues from the catalysts can dissolve in the glyceride composition, typically in amount of 1–10 mg/g. Metals can act as unwanted catalysts for oxidation. Also, a purified product is not expected to contain residues from catalysts, and the health effects of any such residues should be documented.

In view of the state of the art it would be desirable to be able to provide a simple, effective process for removing at least some of the impurities which are commonly found in polyunsaturated fatty acid glycerides.

In accordance with the present invention there is provided a process for purifying a composition containing polyunsaturated fatty acid glycerides, comprising subjecting said composition to supercritical fluid fractionation in one or more countercurrent columns operated either with internal reflux achieved by a temperature gradient along the column or with an external reflux achieved through external regulation of the pressure, the solvent for said extraction being a mixture of supercritical $CO_2$ and a polar co-solvent; and recovering a purified composition containing said polyunsaturated fatty acid glycerides.

As is well known, it is possible to change from one state of a pure compound (i.e. solid, liquid or gaseous) to another state by changing the temperature and/or pressure of the compound. It is also well known that there exists a value, termed the "critical value" of temperature and/or pressure beyond which it is impossible to pass from the liquid state to the gaseous state without ebullition and in the reverse direction without condensation in a continuous manner.

It is known that a fluid in supercritical state, i.e. in a state characterized either by a pressure and a temperature respectively higher than the critical pressure and temperature in the case of a pure compound, or by a representative point (pressure, temperature) located beyond the critical point envelop curve represented on a (pressure, temperature) diagram in the case of a mixture of components, exhibits a high solvent power for many substances, much higher than that observed with the same fluid in a compressed gas state. The same behaviour is observed with "subcritical" liquids, i.e. liquids in a state characterized either by a pressure higher than the critical pressure and a temperature lower than the critical temperature, in the case of a pure compound, or by a pressure higher than the critical pressure and a temperature lower than the critical temperature of the components in the case of a mixture of components (see in the journal "Informations Chimie" No. 321, October 1991, pages 166–177 of the article of Michel PERRUT, entitled "Les Fluides Supercritiques, applications en abondance").

The important and controllable variations of the solvent power of such fluids in a supercritical state are used in many processes: extraction (solid/fluid), fractionation (liquid/fluid), analytical and preparative elution chromatography, and material treatment (ceramics, polymers, etc); chemical or biochemical reactions are also conducted in such solvents.

One of the principal advantages offered by processes using fluids at a supercritical pressure consists in the easy separation between solvent (the fluid) and the extracts and solutes, as has been described in numerous publications.

It has been known for a long time that it is possible to fractionate vegetable or animal oils on countercurrent columns using supercritical fluids, especially carbon dioxide or carbon dioxide mixed with an organic solvent such as propane, hexane and alcohols. A recently published book edited by J. W. King and G. R. List "Supercritical Fluid Technology in Oil and Lipid Chemistry", AOCS Press, Champaign, Ill., USA, 1996 provides a comprehensive review of the published work in this area. Chapter 8, "Supercritical Fluid Extraction and Fractionation of Fish Oils" by W. B. Nilsson, in particular, gives a useful account of the state of the art relevant to the present invention.

It is an advantage of the process of the present invention that it is very flexible. Thus, according to the operating parameters selected it is possible to remove either oligomeric/polymeric mixtures, or malodorous components, or both, and also the process can incorporate a step of fractionating the glyceride components, as will be described below. Accordingly, the product obtained from the supercritical fractionation can readily be altered at will by appropriate selection of the operating conditions.

In one preferred embodiment of the present invention, a glyceride composition which has been subjected to purification treatment by the present process is then subjected to further supercritical fluid fractionation in one or more countercurrent columns operated either with internal reflux achieved by a temperature gradient along the column or with an external reflux achieved through external regulation of the pressure using as solvent a mixture of supercritical $CO_2$ and a polar solvent, and the fractionation conditions being controlled so as to favor fractionation of the glyceride components, whereby there is recovered a triglyceride-enriched fraction and a fraction enriched in mono- and diglycerides.

In another embodiment of the present invention, a glyceride composition which has been subjected to removal of mono- and diglycerides is then subjected to purification by means of the process of the present invention in order to remove polymeric material.

Achieving fractionation of the glyceride components requires a higher selectivity than is needed for removal of oligomers. Accordingly, it is preferred to use conditions leading to a lower solubility of the glycerides in the solvent. Thus, it is preferred to operate the fractionation column at a pressure lower than that used in the column or columns in which the purification step is conducted (typically from 100–250 bar, preferably 120–180 bar), and at a temperature at least as high, and preferably greater than in the purification step, and with a similar or lower co-solvent concentration in the extraction solvent. Typically, the temperature gradient ranges from 30°–40° C. (bottom) to 60°–80° C. (top), and the co-solvent, preferably ethanol, is present at a concentration of 5–20% by weight, preferably 5–10% by weight.

In yet another preferred embodiment of the present invention, the glyceride composition is subjected to at least two supercritical fractionations in accordance with the teachings of this invention, with the operating conditions in one fractionation being selected to favor removal of oligomeric/polymeric impurities, and those in a second fractionation being selected so as to favor removal of malodorous components.

As mentioned above, the solvent used in the supercritical fractionation of this invention is a mixture of supercritical $CO_2$ and a polar solvent. By "polar solvent" is meant any organic solvent which is more polar than unsubstituted saturated hydrocarbons. Examples of suitable polar solvents for use herein are lower alcohols, such as $C_{1-4}$ alcohols, and lower ketones such as $C_2$–$C_4$ ketones. Preferred polar co-solvents for use herein are ethanol and acetone, with ethanol often being preferred because of its low toxicity. The presence of the polar co-solvent significantly increases the solvent power of the supercritical $CO_2$, whereby the total amount of solvent that has to be employed can be reduced.

The relative proportions of supercritical $CO_2$ to polar co-solvent are not critical, but often the weight ratio of supercritical $CO_2$ to polar co-solvent will be from 99:1 to 80:20, and preferably from 95:5 to 90:10.

Another important feature of the supercritical fractionation process of the present invention, leading to enhanced selectivity, is that it is conducted either with an internal reflux in the column which is achieved by providing a temperature gradient therealong, or with an external reflux which is achieved through external regulation of the pressure.

As the solubility of glycerides decreases with increasing temperature of the solvent mixture, (for supercritical fluids, solubility usually increases with increasing density and thus decreases with increasing temperature) the provision of a temperature gradient along the column, with the temperature rising up the column, has the effect that some of the components which are initially solubilized when the glyceride composition is introduced into the column are carried towards the top of the column in solution. However, as the temperature progressively rises these components then come out of solution again and through the action of gravity travel down towards the bottom of the column where they are partly re-solubilized. Thus, the provision of the internal temperature gradient in the column leads to a reflux effect which results in a better separation of impurities from the glyceride composition. For instance, as shown in Examples 1 and 2 below the provision of internal reflux leads to the fraction recovered from the top of the column being substantially free of the less soluble oligomeric impurities.

Similarly, the provision of external reflux also leads to higher fractionation selectivity. External reflux is achieved by reducing somewhat the pressure of the extract withdrawn from the upper end of the fractionation column, whereby those components of the extract which have the lowest solubility in the $CO_2$ solvent are caused to precipitate out. In order to bring the precipitated components back to the fractionation column, preferably being reintroduced to the upper part of the column, the pressure is returned to a higher level, for example by means of a high pressure pump.

The use of external reflux will often be preferred over internal reflux for larger diameter columns, where it can often be difficult to establish the required temperature gradient along the column.

The present invention may be used to purify a wide range of compositions containing polyunsaturated fatty acid glycerides. It is, however, particularly valuable for the purification of glyceride compositions derived from marine oils, in the preparation of pharmaceutical compositions containing high concentrations of EPA+DHA.

By means of the present invention in preferred cases it is possible to substantially remove more than 90% by weight of all the aforementioned organic and metallic impurities from polyunsaturated fatty acid glyceride compositions.

Figure 2:
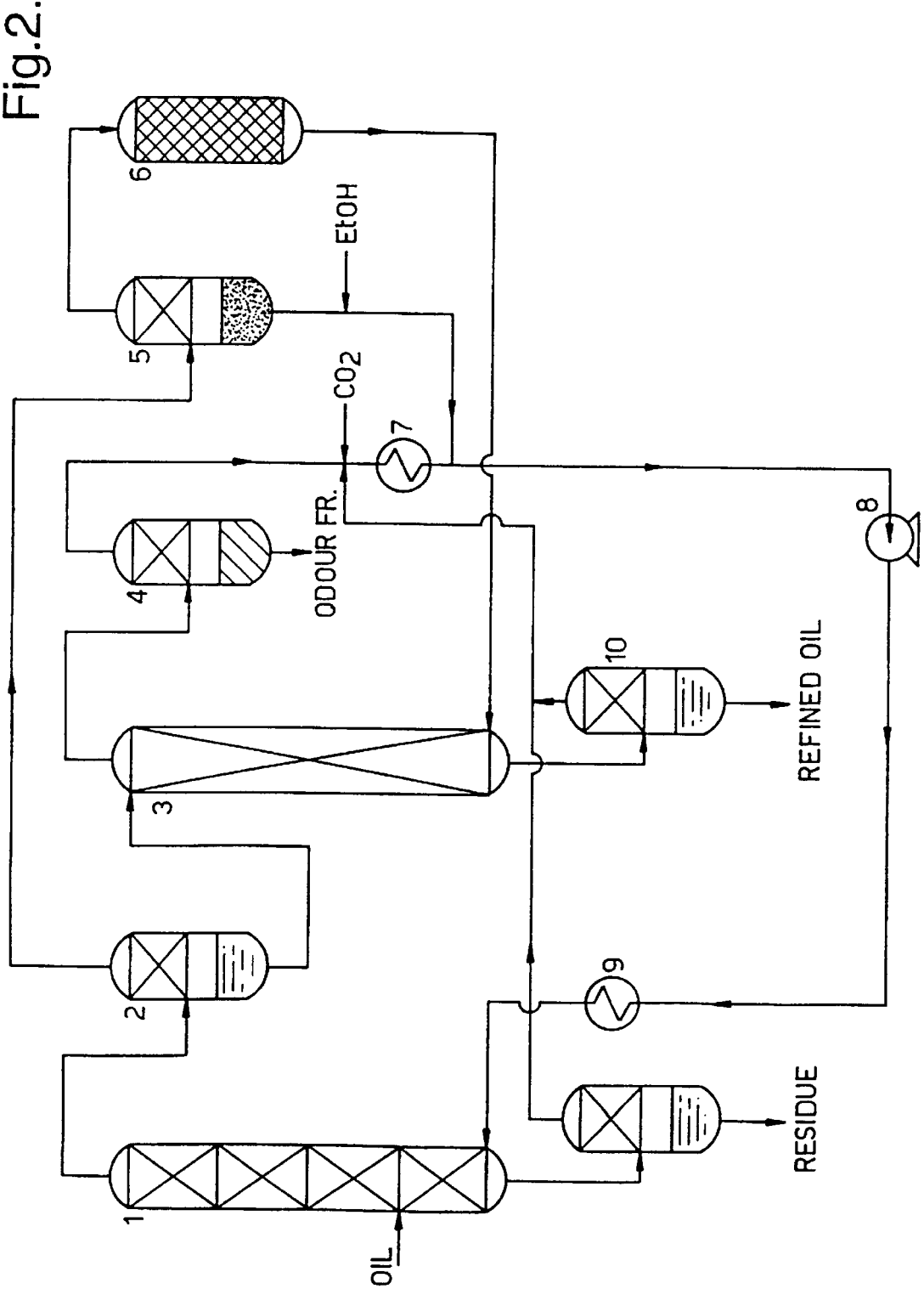
Figure 3:
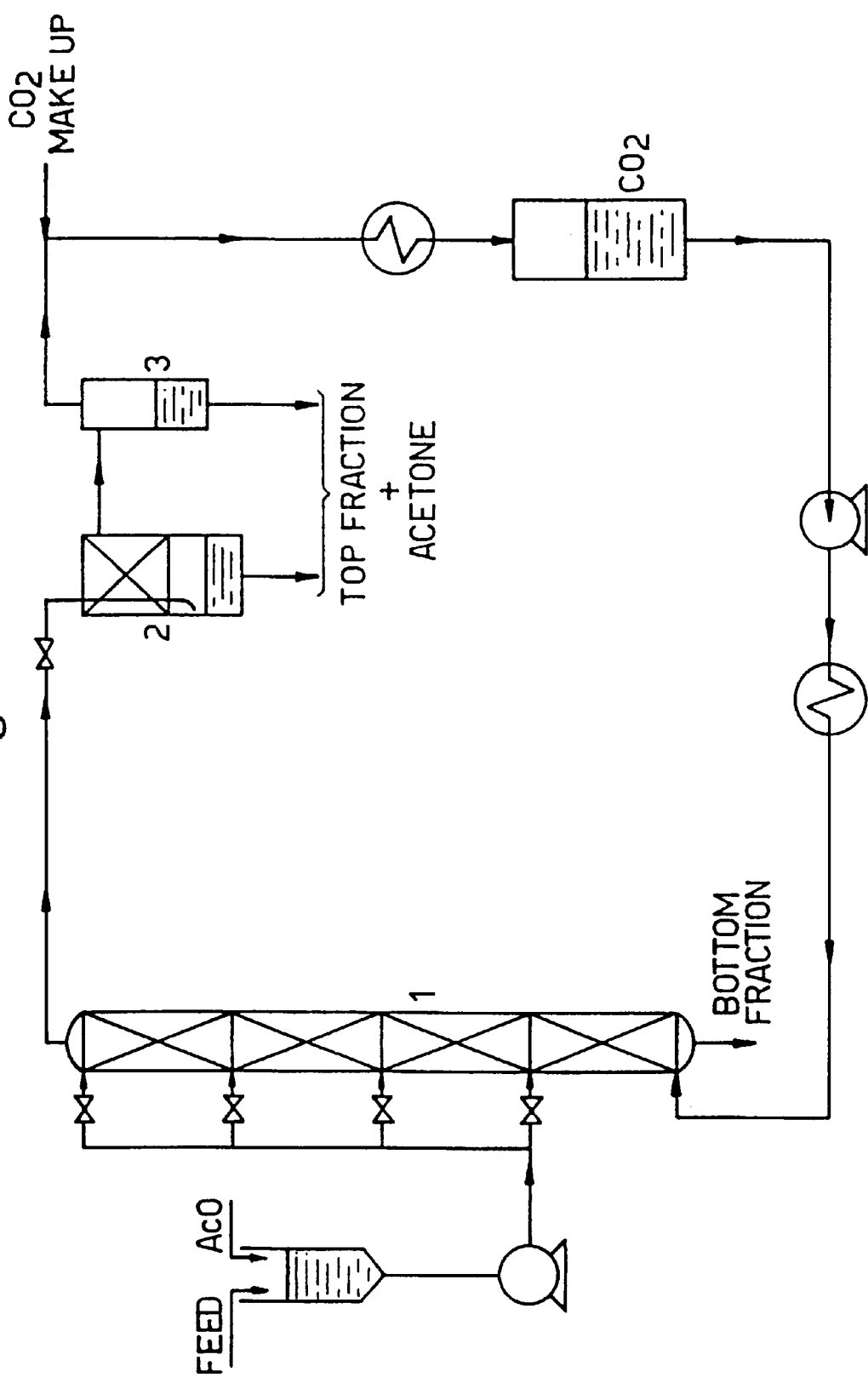
Figure 4:
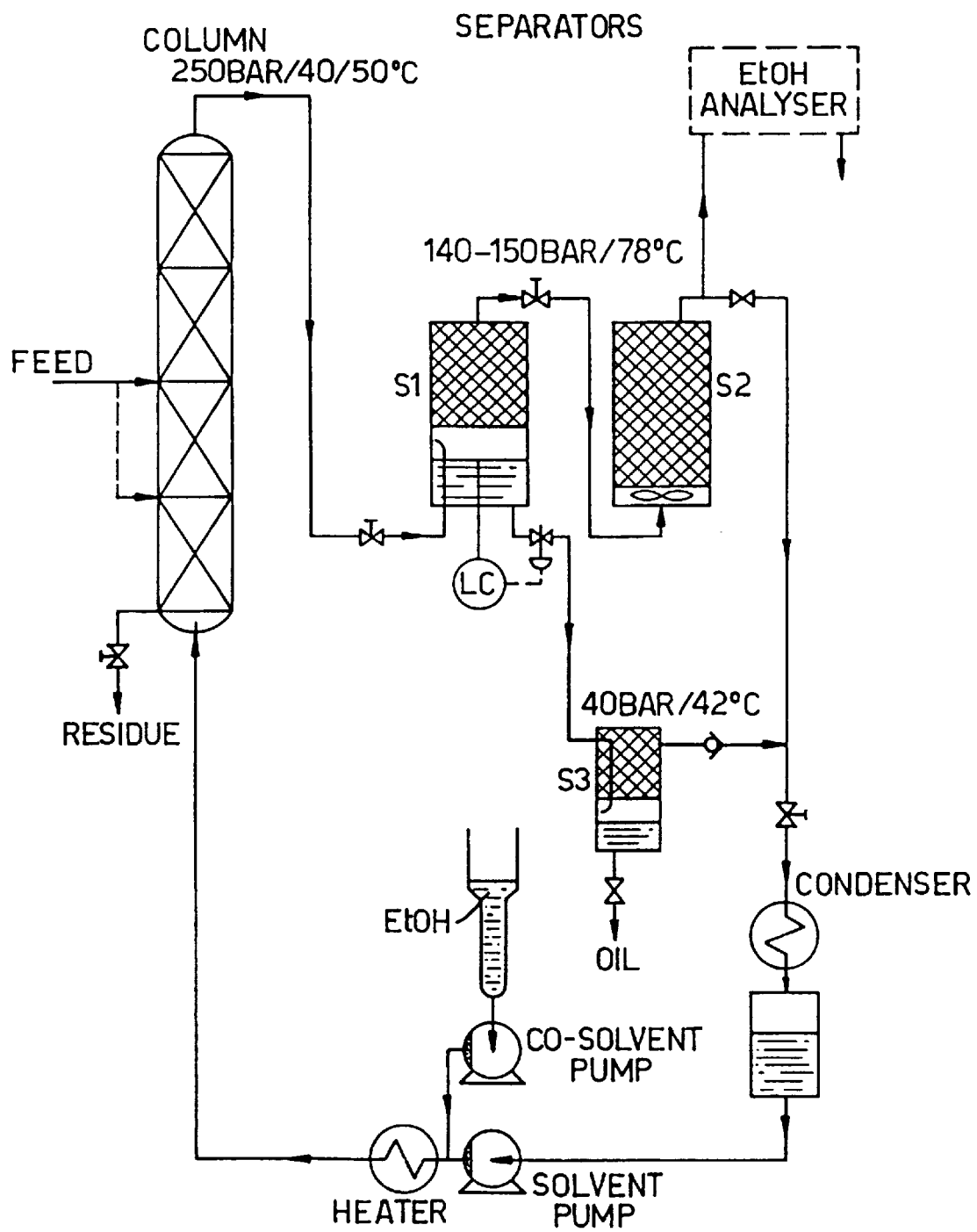
Figure 5:
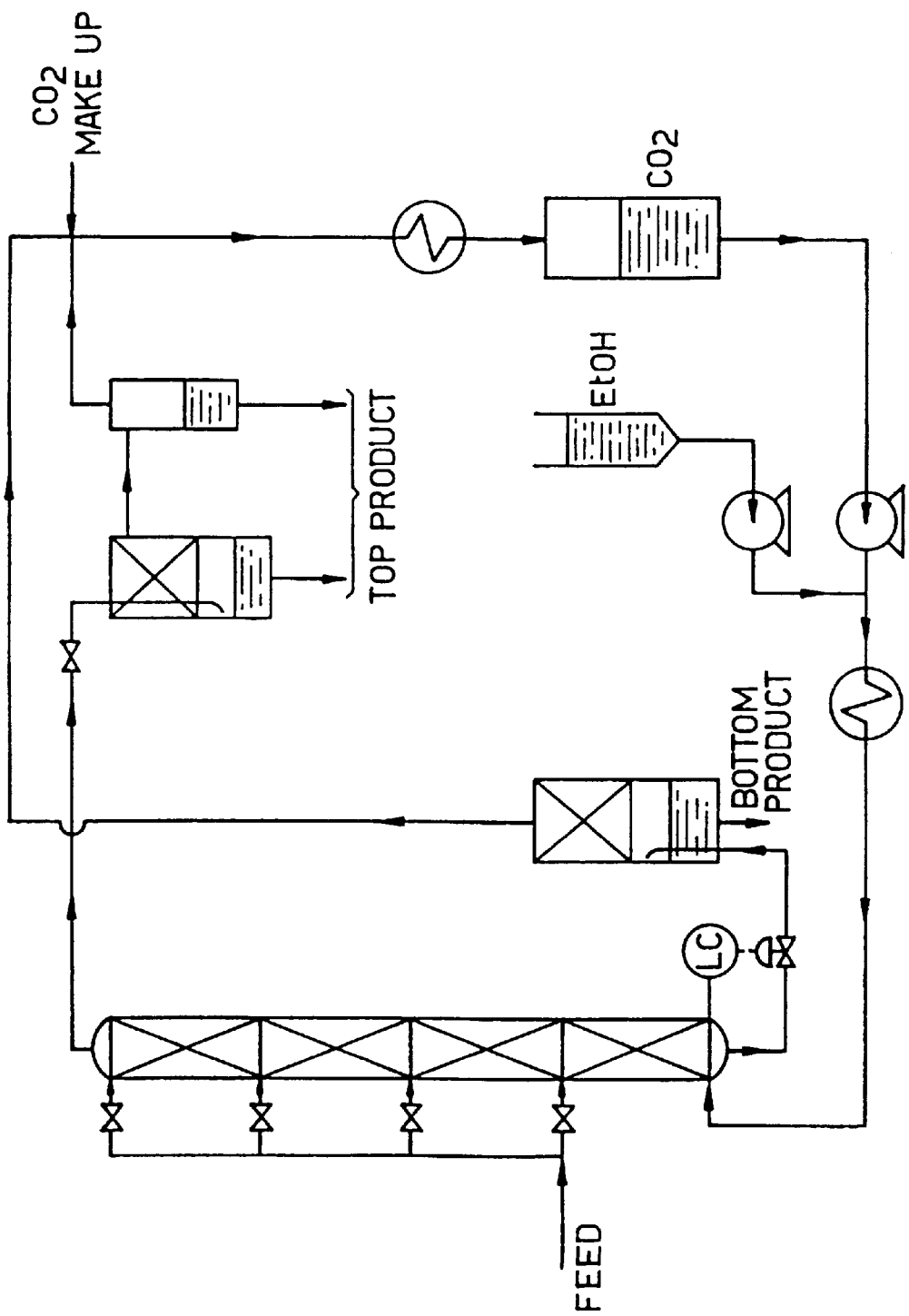
Figure 6:
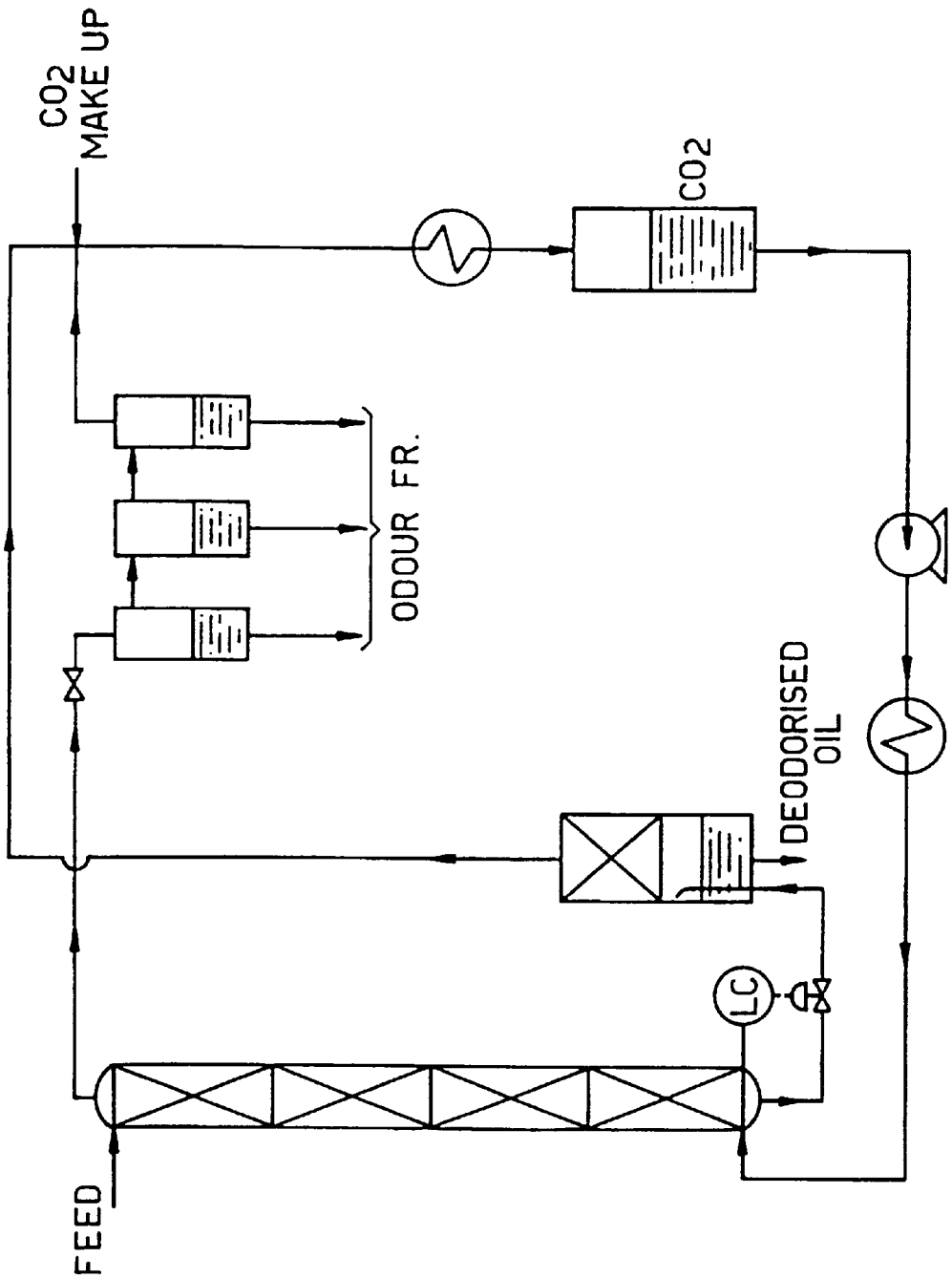

The invention will now be described in more detail with reference to the accompanying drawings, in which:

FIG. 1 is a schematic diagram of a first embodiment of a system for treating a polyunsaturated fatty acid glyceride composition of this invention, FIG. 2 is a schematic diagram of a second embodiment of a system for treating a polyunsaturated fatty acid glyceride composition of this invention, FIG. 3 is a schematic diagram of the system employed in Example 1, FIG. 4 is a schematic diagram of the system employed in Example 2, FIG. 5 is a schematic diagram of the system employed in Example 3, and FIG. 6 is a schematic diagram of the system employed in Example 4.

Referring first to FIG. 1 of the drawings there is schematically shown a system embodying two independent supercritical fluid circuits for treating polyunsaturated fatty acid glycerides in order to remove oligomer and malodorous impurities.

The glyceride composition ("oil") to be treated is pumped into countercurrent fractionation column 1 which, as indicated, contains at least four separately heated sections. The column 1 is filled with inert packing, e.g. glass, PTFE, polyamide, and operates with a temperature gradient ranging from 30°–40° C. (bottom) to 70°–80° C. (top) and a pressure between 150–350 bar, preferably about 250 bar.

Supercritical fluid consisting of $CO_2$+polar co-solvent, preferably ethanol at a concentration of 5–10% by weight, is pressurized by means of a pump 4 and passed through a heater 5 into the lower end of column 1. The upwardly flowing supercritical fluid contacts the falling glyceride composition countercurrently, whereby the lower molecular weight compounds including the desired glycerides are enriched in the fluid. Similarly, the higher molecular weight species, including the unwanted oligomers, concentrate in the liquid phase leaving the bottom of column 1 via expansion vessel 6.

The existence in the column 1 of the temperature gradient provides an internal reflux which causes higher molecular weight components of the solute, especially oligomers, to precipitate and thus increases the selectivity of fractionation. A similar effect can be obtained by causing reflux of the extract by external regulation of the pressure using a pump.

Supercritical fluid leaving the top of the column 1 is expanded to 100 to 200 bar, preferably near 150 bar, and heated up to 60°–80° C. in a vessel 2. Under these conditions, the glyceride fraction is precipitated from the supercritical phase of $CO_2$+co-solvent which is recycled via a cooler 3, pump 4 and heater 5 to the column 1.

The glyceride composition from vessel 2 containing up to 20% of ethanol co-solvent, is then fed into the top of a second packed column 6 operated at 120–150 bar and temperature of 50°–70° C., where it is countercurrently contacted with pure supercritical $CO_2$ which preferentially entrains volatile compounds (odours) as well as co-solvent remaining in the glyceride composition.

Volatile fraction-laden $CO_2$ is routed via an expansion vessel 7 at a pressure of 40–60 bar where most of the volatile components are precipitated, an adsorption vessel 8 filled with activated charcoal to remove traces of volatiles, a cooler 9, a pump 10, a heater 11 and then, finally, is recycled to the column 6.

The purified liquid exiting from the bottom of column 6 is expanded in vessel 12 to 40–60 bar and to 1 bar in vessel 13 and the $CO_2$ from the first decompression vessel 12 is recirculated to cooler 9.

Compared with a typical procedure of supercritical extraction with co-solvent including combined precipitation of extract+co-solvent, the proposed process offers several important advantages. As the glyceride composition from vessel 2 contains up to 20% ethanol as co-solvent, it is unnecessary to add co-solvent to the $CO_2$ that is used in column 6. The pure $CO_2$ in column 6 dissolves the co-solvent from the glyceride composition, and thus increases the solubility of the volatile compounds (odours). As the co-solvent is removed together with the volatile components, no costly distillation unit is needed in order to remove the co-solvent from the product, thus simplifying the process, and reducing the thermal treatment of the product which is required.

Referring now to FIG. 2, there is shown schematically a system for purifying a polyunsaturated fatty acid glyceride composition in accordance with this invention using a single supercritical fluid circuit.

As in the system shown in FIG. 1, the glyceride composition is initially treated in fractionation column 1 with a countercurrent flow of supercritical fluid, preferably $CO_2$+ethanol, which is then led to an expansion vessel 2 to precipitate out the glyceride phase.

Thereafter, the supercritical phase of $CO_2$+co-solvent leaving vessel 2 is once more expanded to 100–400 bar, preferably about 120 bar, in a vessel 5 to precipitate ethanol from the supercritical phase of $CO_2$. Supercritical $CO_2$, stripped of co-solvent, is purified in a charcoal absorption bed in a vessel 6, and then enters column 3 where, as in column 6 of FIG. 1, it flows countercurrently to the glyceride fraction withdrawn from expansion vessel 2 and extraction of the malodorous volatile compounds occurs. The column operates at a constant temperature of 50°–70° C., preferably about 60° C., and a pressure of 100–140 bar, preferably about 120 bar. The stream leaving the top of the column 3 is expanded at 40–60 bar into a vessel 4 to precipitate malodorous volatiles and remaining co-solvent from the $CO_2$. The gaseous $CO_2$ which is liberated in vessel 4 is condensed in a cooler 7, mixed with co-solvent recycled from vessel 5 and recirculated by means of a pump 8 through a heater 9 back into the column 1.

The purified glyceride composition is withdrawn from vessel 10.

It will be appreciated that, compared with the system of FIG. 1, the arrangement of FIG. 2 requires only one cooling/pumping system, thereby effecting considerable capital and operating costs. Nonetheless, the system can, like that of FIG. 1, be used to remove both oligomeric and malodorous impurities from glyceride compositions.

The invention will now be illustrated by the Examples which follow:

EXAMPLE 1

This example illustrates the separation of oligomers from synthetic polyunsaturated fatty acid glycerides using a supercritical fluid composed of $CO_2$ and acetone co-solvent, without co-solvent regeneration. A single multistage column was used and extract and co-solvent fluid separation are achieved under subcritical conditions.

The apparatus employed is shown schematically in FIG. 3.

A 4.5 m long, 8 mm-internal diameter stainless steel column 1 filled with glass Rashig rings was employed. The column 1 was arranged in four sections heated by different baths, resulting in a temperature gradient from 40° C. at the bottom to 78° C. at the top of the column.

A fish oil (EPAX-5500), available from PRONOVA and characterized as shown in Table 1 was used.

|  |  | Analysis |
|---|---|---|
| General |  |  |
| Acid value | mg KOH/g | 2.2 |
| Iodine value | gI/100 g | 322.4 |
| Saponification value | mg KOH/g | 169.2 |
| Unsaponification value |  | 1.4 |
| Peroxide value | meq/kg | 4.4 |
| Cholesterol | mg/g | 6.6 |
| Colour Gardner |  | 5.7 |
| Fatty acid composition |  |  |
| Total ω-3 | A % | 70.8 |
| EPA | A % | 34.0 |
| DHA | A % | 23.8 |
| Total EPA and DHA | A % | 57.8 |
| Tocopherols |  |  |
| Mixed nat. tocopherols* | mg/g | 3.5 |
| Others |  |  |
| Refractive index | 20° C. | 1.5020 |

*Added as 1.42 mg/g Coviox T-70 (Henkel) and 3 mg/g Covitol F-1000 (Henkel)

2 kg of the oil was mixed with 8 kg acetone of technical grade and fed into the first stage of the column (temperature 40° C.). The column was operated on continuous mode at 250 bar using the following loading:

feed flow rate=0.38 kg/h $CO_2$ flow rate=20.3 kg/h acetone content in $CO_2$=6.5 wt %

The product from the top of the column, containing purified oil and acetone dissolved in supercritical $CO_2$ was expanded in vessel 2 into subcritical conditions (20° C., 50 bar) to precipitate co-solvent and extract. After acetone vaporization in vessel 3, 1.34 kg of oil (extraction yield 67%) was recovered. Both the top and bottom fractions were subjected to the analysis for polymers/glycerides content by gel permeation chromatography (GPC). The results are shown in Table 2:

TABLE 2

| | (Area %) | | | | |
|---|---|---|---|---|---|
| Sample | Oligomers | TG | DG | MG | FFA |
| Top fraction | — | 32.6 | 52.5 | 12.9 | 1.9 |
| Bottom fraction | 5.6 | 72.4 | 20.4 | 0.6 | 1.0 |

From the data in Table 2, it can be seen that the process of oligomer separation is highly effective; the oil from the top is in practice free of heavy, undesirable oligomeric products.

EXAMPLE 2

This example illustrates the separation of oligomers from the fish oil EPAX-5500 which was utilized in Example 1, on a multistage countercurrent column using a supercritical fluid composed of $CO_2$ and ethanol, with co-solvent recovery and recycling.

The equipment employed is shown schematically in FIG. 4; it will be seen that it is similar to that shown in FIG. 1. The column 1 was equipped with three separators operated at different levels of pressure and temperature.

The system was first filled with $CO_2$ and then the high pressure pump was operated. The operating conditions were as follows:

|  | Temp (° C.) | Pressure (bar) |
|---|---|---|
| Column | 40 (bottom)/50 (top) | 250 |
| Separators 1 + 2 | 78 | 150 |
| Separator 3 | 40 | 50 | feed flow rate=0.57 kg/h solvent flow rate=24.6 kg/h 1.5 kg of ethanol (fermentation-grade) was added to the circulating $CO_2$. After 2 hours, when the content of ethanol in $CO_2$ was stabilized at the level of 7 wt %, 3 kg of the fish oil was fed into the second stage of the column. Oil-laden fluid leaving the top of the column was introduced into the separator S1 where the oil fraction was precipitated; the carbon dioxide+ethanol remained in the supercritical state; this stream of $CO_2$ with entrainer leaving separator S1 was passed through vessel S2 filled with glass packing to remove oil droplets and then recycled to the column.

Liquid phase from S1 was expanded in separator S3 to decrease the $CO_2$ content. The ethanol concentration in the products was as follows:

extract (S3): 8.8% residue (column): 8.9%

TABLE 3

| Sample | Oligomers | TG | DG | MG | FFA |
|---|---|---|---|---|---|
| | (Area %) | | | | |
| Extract (83%) | 0.15 | 40.8 | 46.4 | 10.6 | 2.0 |
| Residue (17%) | 10.1 | 69.6 | 19.9 | 0.4 | — |

As can be seen from Table 3, fish oil processing with ethanol as a co-solvent was just as effective in removing oligomeric impurities as the process described in Example 1. Furthermore, this process, with co-solvent recovery and recycling, yields products much less contaminated by ethanol which can, if desired, be easily stripped by $CO_2$ in an oil deodorization step such as is illustrated in Example 4.

EXAMPLE 3

This example illustrates the subsequent treatment of purified triglyceride composition by the process of the invention to recover a triglyceride-enriched fraction and a mono- and diglyceride-enriched fraction.

The apparatus used is schematically illustrated in FIG. 5.

A multistage column, similar to that employed in Example 1, was operated under the following conditions:

temperature gradient 40° C. (bottom)/50/65/78° C. (top)
pressure=150 bar
solvent/feed ratio=88 kg/kg
feed flow rate=0.275 kg/h
solvent flow rate=24.2 kg/h 688 g of fish oil, subjected to preliminary removal of oligomers by a process similar to Example 2 was fed to the second stage of the column. Ethanol and $Co_2$ were premixed in the proportions corresponding to co-solvent concentration of 10 wt %. Of the initial feed, 66% was withdrawn at the bottom of the column and 34%, as a mixture with $CO_2$+ethanol, left the top of the column and then passed through two separators (20° C./50 bar) to precipitate a glyceride fraction+ethanol and to liberate gaseous $CO_2$.

The contents of glycerides in the initial oil and in the two fractions obtained were evaluated by HPLC with a refractive index detector. The results are shown in Table 4.

TABLE 4

| Sample | TG | DG | MG |
|---|---|---|---|
| | (Area %) | | |
| Feed | 67 | 27 | 6 |
| Top Fraction (34%) | 4 | 63 | 33 |
| Bottom Fraction (66%) | 89 | 10 | 1 |

These analytical data show that the experiment achieved good separation of triglycerides from di- and mono-glycerides, the bottom fraction consisting of triglycerides.

This example, as well as Example 2, illustrates the flexibility of supercritical fluid processing of glycerides of fatty acids derived from marine oils when using the same binary solvent, $Co_2$+ethanol, and changing only the operation parameters of the column: separation of oligomers as well as glyceride fractionation can be achieved.

EXAMPLE 4

This example illustrates the purification of fish oil on a multistage column under conditions favourable to remove the malodorous impurities.

The equipment used is schematically shown in FIG. 6.

A multistage column, as in Example 1, was operated under the following conditions:

temperature gradient=50° C. (bottom)/55/60/70° C. (top)
pressure=120 bar
$CO_2$/feed ratio=38
feed flow rate 0.645 kg/h
$CO_2$ flow rate=24.5 kg.h 1.2 kg of fish oil (EPAX 5500) was fed into the top of the column and contacted countercurrently with supercritical carbon dioxide flowing from the bottom. Preferentially entrained volatile compounds were dissolved in $CO_2$ and left the top of the column. This odour fraction-laden $CO_2$ was first expanded into 3 cyclonic separators (80/70/50 bar/20° C.) to precipitate liquid extract and then passed through a two liter vessel filled with activated charcoal to remove traces of volatiles from $CO_2$. Carbon dioxide leaving charcoal bed was, after liquefaction, recycled to the column.

1.16 kg of oil was withdrawn at the bottom (recovery~97%) The results of GC analysis show imperceptible concentrations of volatile compounds in the refined product and the fish odour had totally disappeared.

EXAMPLE 5

This example illustrates the separation of metal compounds from a glyceride composition. The equipment employed was identical to that used in Example 2.

Before extraction, the glyceride had been in contact with zinc oxide power (catalyst for esterification). After the esterification reaction was terminated, some zinc remained in solution. The exact chemical composition of the dissolved zinc was unclear, but the zinc could possibly have been present as soaps or possibly as complexes with fatty acid double bonds. Before the extraction started, undissolved powder was removed by filtering.

The column was operated at 250 bar and at a temperature gradient from 40–60° C. The feed flow rate was 0.5 kg/h, and the solvent flow rate 25 kg/h. The content of ethanol in the solvent was 6.5%.

As in Example 2, the oligomers were concentrated in the residue (18% in the residue and below detection limit in the extract). At the same time, zinc was concentrated in the residue:

| | Zn (mg/g) |
|---|---|
| Extract (87%) | 0.034 |
| Residue (13%) | 5.6 |

These results demonstrate that the present invention represents an excellent process for the removal of metal contaminants from glycerides.

EXAMPLE 6

This example illustrates the use of external reflux.

The process and apparatus are generally similar to that of Example 2 and FIG. 4 except that the temperatures in the column jackets are set to be uniform at 40° C. A high pressure pump recompresses part of the liquid collected in vessel 51 (150 bar, 78° C.) that is recycled at the top of the column, at a flowrate of 0.1 kg.h$^{-1}$.

External reflux achieves very similar results in terms of productivity, yield and purity to those obtained with internal reflux.

What is claimed is:

1. A process for purifying a starting glyceride composition containing a mixture of different polyunsaturated fatty acid glycerides together with at least one impurity, comprising the steps of:

(a) subjecting said composition to supercritical fluid fractionation in one or more countercurrent columns in which the fluid serves to extract at least a portion of at least one impurity from the composition, the column being operated either with internal reflux achieved by a temperature gradient along the column or with an external reflux achieved through external regulation of the pressure, and the fluid for said extraction being a mixture of supercritical $CO_2$ and a polar co-solvent; and (b) recovering a purified composition containing said polyunsaturated fatty acid glycerides with a lesser concentration of impurities than was present in said starting composition.

2. A process according to claim 1, wherein said polar co-solvent is ethanol or acetone.

3. A process according to claim 1 or claim 2, wherein the weight ratio of said supercritical $Co_2$ to said polar co-solvent is from 99:1 to 80:20.

4. A process according to claim 3, which is operated so as to preferentially remove oligomeric/polymeric impurities from said glyceride composition.

5. A process according to claim 3, which is operated so as to preferentially remove metal impurities from said glyceride composition.

6. A process according to claim 3, which is operated so as to preferentially remove malodorous components from said glyceride composition.

7. A process according to claim 3, wherein said starting glyceride composition contains mono-, di-, and triglycerides and said purified composition which is recovered contains one or more unextracted impurities and is subjected to a supercritical fluid fractionation in one or more countercurrent columns in which the fluid serves to extract at least a portion of at least one said impurity from the composition, the column being operated either with internal reflux achieved by a temperature gradient along the column or with an external reflux achieved through external regulation of the pressure, and the fluid for said extraction being a mixture of supercritical $Co_2$ and a polar co-solvent, and the fractionation conditions being controlled so as to favor fractionation of the glyceride components, whereby there is recovered a first fraction enriched in triglycerides and a second fraction enriched in mono- and diglycerides.

8. A process according to claim 1 or 2, wherein said starting glyceride composition is (i) derived from a marine oil, (ii) contains at least one oligomeric/polymeric impurity and at least one malodorous component that is not an oligomeric/polymeric impurity, and (iii) is subjected to said supercritical fluid fractionation in at least two countercurrent columns, the operating conditions in one said column being selected so as to preferentially remove oligomeric/polymeric impurities and the operating conditions in another said column being selected so as to preferentially remove malodorous components.

9. A process according to claim 8, wherein the solvent in said another column consists essentially of supercritical $CO_2$.

10. A process according to claim 3, wherein said starting composition is (i) derived from a marine oil, (ii) contains at least one oligomeric/polymeric impurity and at least one malodorous component that is not an oligomeric/polymeric impurity, and (iii) is subjected to said supercritical fluid fractionation in at least two countercurrent columns, the operating conditions in one said column being selected so as to preferentially remove oligomeric/polymeric impurities and the operating conditions in another said column being selected so as to preferentially remove malodorous components.

11. A process according to claim 10, wherein the solvent in said another column consists essentially of supercritical $CO_2$.

12. A process according to claim 1 or 2, which is operated so as to preferentially remove oligomeric/polymeric impurities from said glyceride composition.

13. A process according to claim 1 or 2, which is operated so as to preferentially remove metal impurities from said glyceride composition.

14. A process according to claim 1 or 2, which is operated so as to preferentially remove malodorous components from said glyceride composition.

15. A process according to claim 1 or 2, wherein said starting glyceride composition contains mono-, di-, and triglycerides and said purified composition that is recovered contains one or more unextracted impurities and is subjected to a supercritical fluid fractionation in one or more countercurrent columns in which the fluid serves to extract at least a portion of at least one said impurity from the composition, the column being operated either with internal reflux achieved by a temperature gradient along the column or with an external reflux achieved through external regulation of the pressure, and the fluid for said extraction being a mixture of supercritical $Co_2$ and a polar co-solvent, and the fractionation conditions being controlled so as to favor fractionation of the glyceride components, whereby there is recovered a first fraction enriched in triglycerides and a second fraction enriched in mono- and diglycerides.

\* \* \* \* \*

UNITED STATES PATENT AND TRADEMARK OFFICE
CERTIFICATE OF CORRECTION

PATENT NO.    : 6,204,401 B1
DATED         : March 20, 2001
INVENTOR(S)   : Perrut et al.

It is certified that error appears in the above-identified patent and that said Letters Patent is hereby corrected as shown below:

Title page,
Item [57], Abstract,
Line 11, "C0$_2$" should read -- $CO_2$ --.

Column 9,
Lines 34 and 60, "Co$_2$" should read -- $CO_2$ --.

Column 11,
Lines 18 and 40, "Co$_2$" should read -- $CO_2$ --.

Column 12,
Line 43, "Co$_2$" should read -- $CO_2$ --.

Signed and Sealed this

Fourth Day of December, 2001

*Attest:*

NICHOLAS P. GODICI
*Attesting Officer*  *Acting Director of the United States Patent and Trademark Office*